United States Patent [19]

Cercone et al.

[11] Patent Number: 5,466,231
[45] Date of Patent: Nov. 14, 1995

[54] LAMINATED SPONGE DEVICE

[75] Inventors: Ronald J. Cercone, East Lyme, Conn.;
Scott J. Quaratella, Westerly, R.I.;
Arthur A. Gertzman, Woodbridge, Conn.

[73] Assignee: Merocel Corporation, Mystic, Conn.

[21] Appl. No.: 145,515

[22] Filed: Nov. 4, 1993

[51] Int. Cl.⁶ .............................. A61F 13/15; A61F 13/20
[52] U.S. Cl. ..................... 604/369; 604/304; 604/358; 604/378; 602/41; 602/42; 602/43; 602/46; 602/47; 602/58; 602/59
[58] Field of Search ...................... 604/304, 358, 604/369, 378, 381; 602/41–43, 46–48, 58–59; 128/849, 850

[56] References Cited

U.S. PATENT DOCUMENTS

| | | |
|---|---|---|
| 2,284,944 | 6/1942 | Bruning . |
| 3,648,692 | 3/1972 | Wheeler . |
| 3,900,027 | 8/1975 | Keedwell . |
| 3,934,587 | 1/1976 | Gordon . |
| 3,996,936 | 12/1976 | Widlund et al. . |
| 4,023,571 | 5/1977 | Comerford et al. . |
| 4,054,141 | 10/1977 | Schwaiger et al. . |
| 4,102,340 | 7/1978 | Mesek et al. . |
| 4,216,774 | 8/1980 | Graber . |
| 4,292,972 | 10/1981 | Pawelchak et al. . |
| 4,524,474 | 6/1985 | Svensson . |
| 4,664,662 | 5/1987 | Webster ................................. 604/369 |
| 4,925,453 | 5/1990 | Kannankeril . |
| 4,997,425 | 3/1991 | Shioyo et al. . |
| 5,009,652 | 4/1991 | Morgan et al. . |
| 5,147,338 | 9/1992 | Lang et al. ............................. 604/304 |
| 5,336,163 | 8/1994 | Demane et al. ......................... 602/46 |

*Primary Examiner*—Randall L. Green
*Assistant Examiner*—P. Zuttarelli
*Attorney, Agent, or Firm*—Gipple & Hale; John S. Hale

[57] ABSTRACT

A surgical device constructed of a polyvinyl acetal sponge body constructed with an average pore diameter ranging from about 0.02 to about 1.2 mm and opposite sides laminated with a surface film layer of about 0.0015 inches thick. The laminate surface film layer is perforated with a plurality of holes allowing access to the body of the surgical device having a diameter ranging from about 0.1 to about 0.7 mm allowing absorbtion of fluid through the laminate layer into the sponge body of the device.

20 Claims, 2 Drawing Sheets

LAMINATED SPONGE DEVICE

BACKGROUND OF THE INVENTION

1. Field of Invention

The present invention generally relates to medical sponge surface treatments and more specifically is directed towards a sterile cellular synthetic sponge wound dressing or cavity pack made of polyvinyl acetal which has one or more surfaces laminated to form a smooth non-stick surface to assist in the insertion into a wound or wound cavity and subsequent removal from the wound site.

2. Description of the Prior Art

The literature is replete with references to various types of foam materials including polyurethane, polyisocyanate, polystyrene, polyolefin, polyvinyl chloride, epoxy, urea-formaldehyde, latex, silicone, and fluoropolymer and with methods of controlling the foam or sponge density and other bulk properties during manufacture.

Advances in the development of synthetic polymers have produced radical changes in wound care dressings, bandages, and medical sponges. Factors such as water vapor, oxygen permeability, bacterial impermeability, and selective absorption can be incorporated into new formulations. These new formulations also address specific requirements such as conformability, non-adherence, and adhesiveness. Thus, a family of polymeric products has been formed for wound care including polymeric foams, polymeric films, particulate and fibrous polymers, hydrogels and hydrocolloids.

The optimum wound handling characteristics for wound care dressings and bandages are expressed in general terms such as a) removal of excess exudate and toxic components; b) maintaining a high humidity or moistness at the wound/dressing interface; c) allow gaseous exchange; d) providing thermal insulation; e) protecting against secondary infection; f) freeing the wound from particulate contaminants; and g) removal of the dressing from the patient without pain or trauma. Even with the advances in technology, it should be noted that there is no simple dressing or device that can produce the optimum micro environment for all wounds or for all the healing stages of a single wound.

Wound dressings and other packing materials used for nasal, sinus or otic packing require a high degree of absorptivity. They normally will swell as body fluids are absorbed. However, current materials and sponges such as porous foams support the coagulated blood and proteins exuding from the cavity surfaces that have been disrupted by surgery or trauma. These coagulated materials enter the pores of the sponge and dry in place. The dried material has thus formed a connection between the sponge packing and the regenerating tissue surface. When it is necessary to remove these sponges, the sponge can stick to the tissue surface via this connection. Removal of the medical sponge then causes debridement of the healing tissue surface causing pain and occasionally rebleeding.

There are a number of prior art references disclosing sponge dressings having varied treated surfaces.

Topical dressings for burn protection used in absorbing necrotic tissues and exudate are shown by U.S. Pat. No. 3,648,692. The dressing of this patent has a thin wound facing layer of dressing constructed of any of a number of various neutral synthetic reticulated open-cell solid foam or sponge material covered with a barrier membrane. The thickness of the sponge facing layer is noted as being critical (preferably about one-sixteenth of an inch) for positioning of the barrier so that debris, fluids, etc. contained therein are accessible for phagocytic invasion from the body surface. If the layer is too thick, it is noted that segregated exudate located at the interface is not reached by the natural phagocytic action with the undesirable result that infection takes place and spreads within the dressing thereby delaying or preventing the healing process.

Another foam sponge product constructed of lyophilized hydrocolloid foam which is capable of absorbing body exudates is shown in U.S. Pat. No. 4,292,972. The wound dressing is preferably constructed with a thin outer oxygen and vapor-permeable film and a layer of an absorbent adhesive such as hydrogel for adhering the wound dressing to the skin and for acting as a reservoir for wound exudate absorbed therein. A layer of collagen, in the form of a sponge or film is adapted for placement directly on the wound, the collagen layer being of smaller dimensions than the absorbent adhesive layer so that areas of the adhesive layer extending beyond the periphery of the collagen layer can be applied to the skin surrounding the wound to adhere the dressing in place.

U.S. Pat. No. 3,934,587 discloses a solid sheet or film of a polymeric compound containing chemically reactable hydroxyl or amine groups that is reacted in a vapor phase mixture of acid chloride and aldehyde to form a product which is water-repellent on the treated side but water-permeable on the opposite, untreated side. The reactant sheet may be constructed of polyvinyl alcohol.

U.S. Pat. No. 5,009,652 discloses a disposable laminated medical sponge or wipe which has a thin sheet that is impermeable to infectious agents as well as being non-wettable by water and a layer of absorbent material having an area which is smaller than that of the impermeable sheet, laminated to the impermeable sheet. The peripheral edges of the absorbent layer are spaced inwardly from the peripheral edges of the impermeable sheet providing a surrounding rim that consists of the impermeable sheet so that liquid which contacts the layer of absorbent material cannot travel through and over the peripheral edge of the impermeable sheet to reach the opposite side of the impermeable sheet.

U.S. Pat. No. 4,925,453 discloses a medical sponge for use as a wipe to absorb body fluids such as blood which protects the person using the sponge from contact. The sponge is constructed with an absorbent pad covered on one face by a fluid permeable cover sheet and on the other face by a fluid impervious cover sheet, both of the cover sheets enclosing the absorbent pad.

U.S. Pat. No. 4,997,425 discloses using a porous wound dressing including a first sponge layer for contacting a wound and a second surface remote from a wound. The second surface, the surface remote from the wound, has a pore size smaller than the first surface.

U.S. Pat. No. 4,054,141 describes a molded absorptive body including an absorptive layer of hydrophilic fibers and a sheath of the hydrophilic fibers bound together by thermoplastic particles. The absorptive body may be provided with a sheath on all sides or only on part of the body.

U.S. Pat. No. 3,900,027 shows a process for making integral absorbent pad bandages from a non-woven thermal plastic fibrous sheet material. The sheet material is compressed in selected portions to reduce thickness and porosity and to limit an absorbent pad having a greater thickness. The resulting sheet material has a plurality of juxtaposed integral absorbent band packages which can be cut off to contain individual bandages. The thermoplastic fibers are noted as being made of any thermal plastic polymeric material which provides differential melting points. During compressing, thickness of the mat is substantially reduced in selected areas in order to reduce porosity and it is noted that the porosity can be totally eliminated. The porosity is reduced in the areas abutting the absorbent pad area so as to limit the spreading of fluids absorbed in the pad section and confine the fluids to that portion. In the course of the compression, the fibers are bonded together due to the thermoplasticity of the fibers by the application of heat and pressure. The fibers can also be bonded and integrated together by the application of a solvent for the fiber polymer prior to the application of pressure.

In addition to the previously noted patents, there also exists prior art which is directed to an impervious plastic layer or coating secured or adhered to an absorbent layer for various garment liners, diapers, medical pads, sanitary napkins, bedding and the like. In this regard see U.S. Pat. Nos. 4,524,474; 4,216,774; 4,102,340; 4,023,571; 3,996,936; 3,934,587 and 2,284,944.

Thus, there exists the need for a sponge dressing or medical sponge device which has a smooth laminated surface which is advantageous for sponge dressing insertion adjacent to surgical wounds. There is also another need for a medical sponge device which can be easily removed thereby eliminating or reducing uncontrolled mechanical debridement of the wound surface while still allowing removal of exudate from the wound and maintaining moisture at the wound pack interface. A problem that occurs with current dressings and medical packs inserted in the human body is the mechanical debridement of the wound or cavity caused by firm adhesion of the dressing or device to the wound or cavity via ingression of blood components serum, mucous and proteins. If the dressing is left in situ for sufficient time, adhesions and actual connective tissue ingrowth and attachment will occur. This adhesion is caused by fibrin produced by the wound or cavity and subsequent spreading of fibroblasts and capillaries. Frictional and shear forces required by the physician to remove the device are lessened in the case of the smooth, non-porous surface or interface of the present invention.

SUMMARY OF THE INVENTION

The present invention is directed toward pierced or perforated laminated polymeric film layers secured to opposing surfaces of a medical sponge. The sponge has a cellular polyvinyl acetal body with a pore size ranging generally from about 0.004 – to about 1.2 mm, and an absorptive capacity of up to 25 times its own weight in fluid, and a retained holding capacity of 16 times its own weight in fluid as per ASTM D-1117-80 with the laminated surface being a thin layer of medical grade polymeric film.

It is an object of the invention to laminate selected surfaces of polyvinyl acetal medical packing devices or wound dressings by laminating opposing or connected sides of the sponge with a thin layer of medical grade polymeric film. The lamination of a thin polymeric film to the bulk sponge body provides the smooth, non-stick surface while maintaining the base polyvinyl acetal sponge properties that are required for a clinically useful wound dressing or nasal and sinus packings.

It is another object of the invention to provide a laminated sponge device for use with nasal, sinus, otic, anal, cervical and vaginal cavities to minimize tissue attachment while leaving other surfaces of the sponge untreated to allow maximum absorption, and wicking of exudate and fluids.

It is still another object of the invention to treat the surface of a sponge product to form a surface layer which reduces tissue attachment and lessens frictional and shear force required to remove the sponge product from adjacent tissues.

It is yet another object of the invention to provide a laminated smooth surface, so that upon removal when the device is adjacent to healing and regenerating tissue (within a body cavity, but not actually attached), this tissue is not removed.

It is another object of the invention to pierce or perforate or fenestrate selected laminated surfaces of polyvinyl acetal dressings and other sponge products to form a smooth surface layer which is semipermeable to fluids.

It is another object of the invention to polarize selected laminated surfaces of polyvinyl acetal dressings and other medical sponge products to form a smooth, hydrophilic surface layer which is semipermeable to fluids.

In the accompanying drawings, there is shown an illustrative embodiment of the invention from which these and other of objectives, novel features and advantages will be readily apparent.

DETAILED DESCRIPTION OF THE INVENTION

Figure 1:
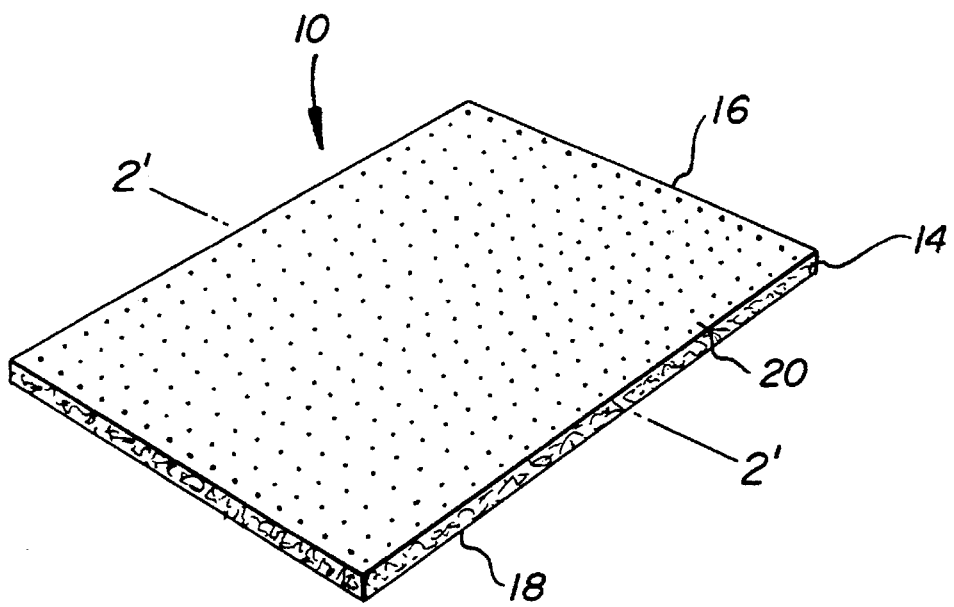
FIG. 1 is a perspective view of a rectangular sponge wound dressing invention.
Figure 2:
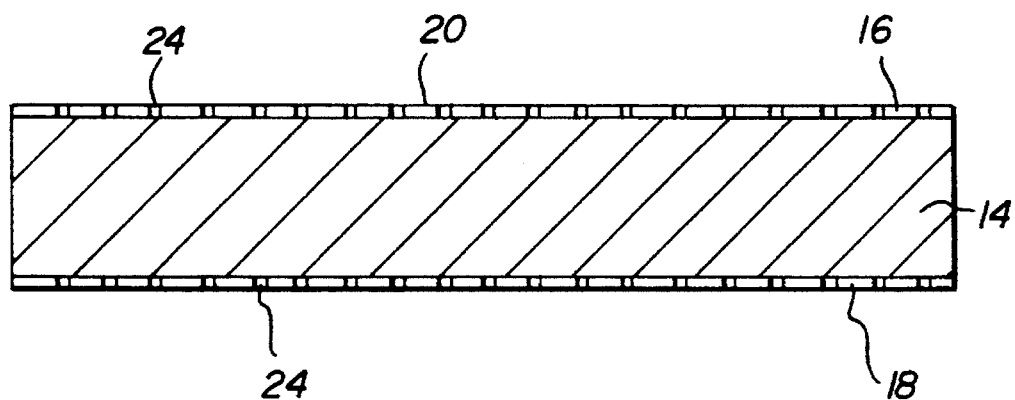
FIG. 2 is an enlarged cross sectional view of the laminated sponge dressing shown in FIG. 1 taken along Line 2'—2'.
Figure 3:
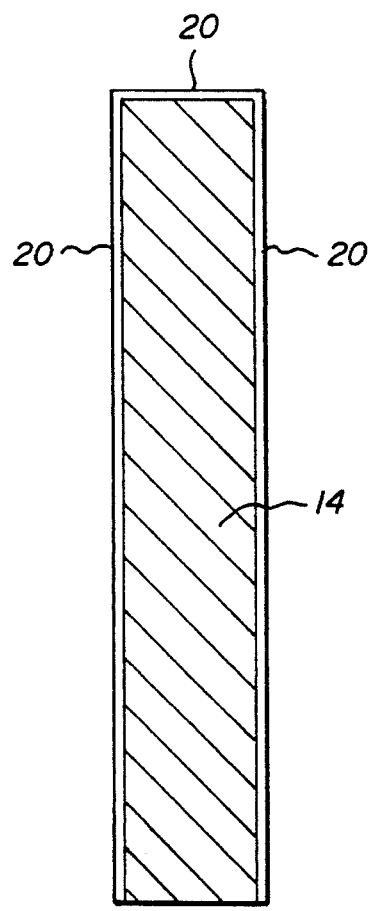
FIG. 3 is an enlarged cross sectional view of an alternative embodiment laminated sponge wound dressing with multiple laminated surfaces.
Figure 4:
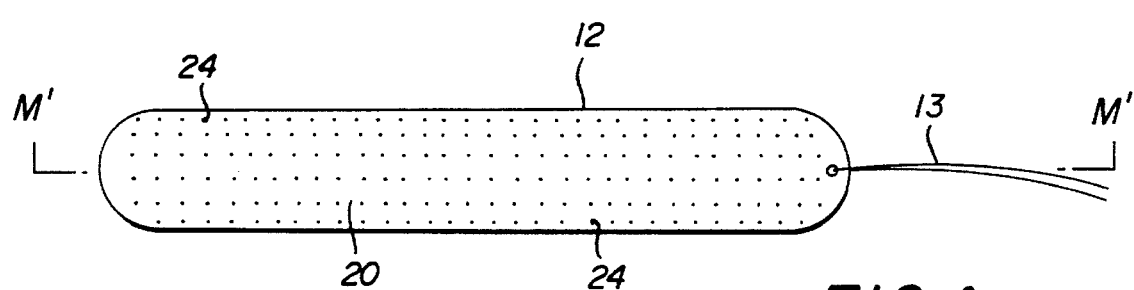
FIG. 4 is a top plan view of a nasal pack embodiment of the invention in a compressed state having a laminated surfaces.
Figure 5:
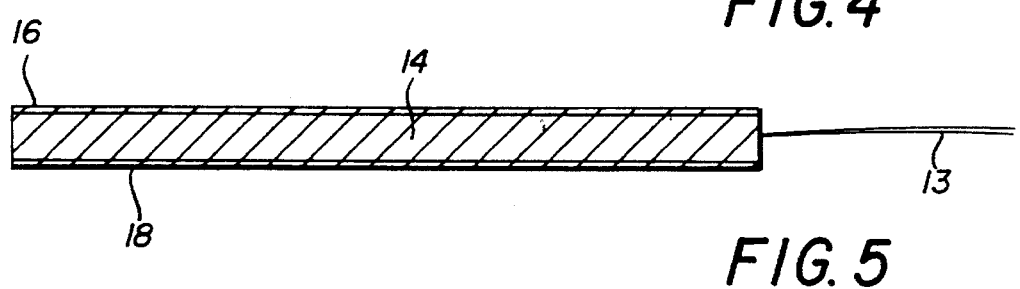
FIG. 5 is an enlarged cross sectional view of the nasal pack of FIG. 4 taken along lines $M^1$—$M^1$.

The preferred embodiment and best mode of the invention is shown in FIGS. 1 and 2. The present medical device is made of a polyvinyl acetal sponge material described in U.S. Pat. No. 4,098,728 issued Jul. 4, 1978. The foam or sponge body of the invention has been fabricated using commercially produced sponge products sold by Merocel Corporation under the grade designations CF50, CF100, CF150 and CF400. These grade designations have respective average pore diameters of 0.95 mm, 0.45 mm, 0.35 mm and 0.2 mm and an overall range of pore diameter of 0.004–1.2 mm. Certain of the grade designates have been used for medical sponges.

The preferred material used is 15 mm thick Merocel CF50 polyvinyl acetal sponge material, a commercially available material manufactured by the Merocel Corporation. The material is a homogeneous white, open-celled sponge with visible pores, instantaneous fluid wicking, absorptive capacity of up 25 times it weight in fluids, a retained fluid capacity of 16 times its own weight in fluids as measured by ASTM D-1117-80, and a pore size range (diameter) of 0.02 to 1.2 mm as determined by Scanning Electron Microscopy at 10× magnification.

The composite sponge dressing 10 or cavity packing 12 has a sponge body 14 as noted above which is laminated on two opposing surfaces 16 and 18 with unsupported acrylic adhesive to a 0.0015 inch thick medical grade polyethylene film 20. The cavity pack 12 is provided with a pull thread 13 secured to one end allowing the pack to be pulled from the cavity it is placed in during treatment. The laminated film 20 is then pierced or fenestrated to create holes 24 through the film and into the sponge body 20 generally less than 1.0 mm diameter and ranging from 0.1 to 0.7 mm. The holes are placed linearly in parallel lines with adjacent holes in the other parallel lines forming transverse lines.

The inventive composite sponge 10 or cavity pack 12 with laminated surfaces exhibits a smooth non-stick surface while maintaining the desired sponge properties of compressibility, conformability, fast wicking, high absorptive capacity and high wet strength. The coefficient of friction for the laminate film surface is lower than for the untreated MEROCEL® sponge material, and provides a minimal opportunity for a three dimensional or geometric interlock with the contacting tissue. The surface is advantageous in reducing or eliminating in-situ attachment of the device to adjacent tissues by preventing tissue attachment. Possible attachment mechanisms which occur between dressings and tissue include adhesions ("a fibrous band or structure by which bodily parts abnormally adhere"), synechiae ("adhesion of body or tissue parts"), and actual tissue ingrowth ("an inward growth of the adjacent tissue"). In addition, removal of the sponge surface past dried blood clots or desiccated mucous is eased by the addition of the smooth laminated film surface.

Lamination is achieved with medical grade adhesives, ultrasonic sealing or melt processing techniques known in the art. Absorption of fluids through the laminated surface(s) can be achieved by appropriate choice of the polymeric film, and treatment of the film through the introduction of slots, crescents or other small openings other than the circular holes as previously noted.

There are many polymeric films, both hydrophilic and hydrophobic, available for laminating to the sponge body. Polyolefins such as polyethylene, halogenated polyolefins such as polytetrafluoroethylene (PTFE), polyesters such as polyethylene terephthalate (PET) and polyurethanes may be used. The polymeric film thickness is specified thick enough to facilitate ease of handling and adequate strength ( to prevent tearing ) while being thin enough, generally in the range of 0.0005 to 0.0030 inches in thickness, to not substantially affect the bulk properties of the sponge in the composite laminated product.

Alternatively, a polymeric film can be laminated to the chosen surface on all but the bottom portions, primarily the lower end or inferior surface such that fluids coming in contact with the laminated surface will naturally drip down the smooth, non-stick surface toward the bottom of the wound or cavity until contact and absorption is made by the unlaminated sponge surface.

Frictional and shear forces required by the physician and experienced by the patient (discomfort, pain) to remove the device are lessened in the case of a laminated surface. The coefficient of friction is not only lower in the treated surface, but there is minimal opportunity for a three dimensional or geometric interlock relative to the direction of device movement required for removal past dried blood clots or desiccated mucous. This also holds true for sponge dressing removal wherein attachment of the device to the adjacent tissues or tissues is reduced.

Use of the inventive sponge device also provides three dimensional stability when increased structure or support is desired.

It may be desirable to support or cause adsorption of some of the wound tissue exudate on the surface of the laminated film. This will prevent excess fluid from running out the nasal cavity. Also, some transmission of fluid and gases ($O_2$) through the hydrophilic laminated film may be needed to support healing at the wound tissue surface. These properties can be achieved by modifying the hydrophobic surface, rendering it hydrophilic to a moderate degree, and supporting adsorption of wound exudate.

The exposed hydrophobic polyethylene surfaces may be generally rendered hydrophilic by polarizing the exposed surface of an otherwise hydrophobic film such as polyolefin. Surface polarization may be achieved by a number of modalities including corona-discharge treatment, plasma treatment, ozone treatment, acid oxidation or other methods known in the art. Polarization will cause liquid droplets to become adherent to the polyethylene surface by ionic bonding of large molecular weight proteins and blood coagulation products onto the surface; this ionic bonding is a secondary and relatively weak force in comparison to the primary attraction via mass transport of aqueous fluids to the untreated sponge. Minimal amounts of fluid, oxygen and any dissolved components (ions, proteins, etc.) may enter the sponge through the laminate surface by diffusion through the thin polymeric film; mass transport modalities are only operable where fluids come directly into contact with untreated sponge. Film surface treatment may be performed on fenestrated or non-fenestrated laminate surfaces.

The entire sponge surface is treated or laminated only in the case where no mass transport of fluids is desired. The great majority of applications for the composite dressing will still benefit by it swelling quickly from its compressed state through absorption of aqueous fluids through the non-laminated surfaces; the resultant swelled product will then exert gentle, even pressure on the inside portion of the wound or body cavity (as does the currently used and commercially available non-laminated sponge dressing).

The present laminated medical sponge invention is constructed by forming the sponge body, slicing or otherwise cutting the sponge body to the desired thickness, placing a layer of acrylic adhesive on the body surface to be covered and then placing the polymeric film layer over the adhesive. The composite is cured. Diecutting of the composite is then performed to produce desired shapes and sizes. The composite product can then be compressed to about ⅛th its original thickness and fenestrated in the desired hole pattern. The laminate product is then packaged into sterile packages.

Fabrication of the inventive laminated sponge device is preferably done by initial formation of composite sheets of the desired thickness followed by die cutting, mechanical compression, fenestration, packaging and sterilization. This method insures a more uniform product, simplifies manufacturing operations and scale-up, and minimizes undesirable product edge effects such as insufficient adhesive application, a lack of an adhesive layer in an area, and overflow of the applied adhesive down onto side sponge body surfaces that are to remain untreated.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. A surgical sponge device for insertion into a body cavity with a wound comprising;

a sterile compressed planar surgical sponge device body constructed of an open cell foam material having a pore diameter size which is not greater than 1.2 mm and having instantaneous wicking properties allowing the body to swell and be free standing inside said cavity, at least two opposing surfaces of said body being laminated with a generally hydrophobic smooth surfaced polymeric film layer having a thickness ranging from 0.0005 to 0.0030 inches for placement against a wound area in said body cavity, said polymeric film layers being pierced with a plurality of holes having a average size not greater than 0.70 mm for fluid absorption providing controlled absorbency into said open cell material and forming a substantially closed outer surface in relation to said open cell foam material reducing tissue attachment and device removal shear forces.

2. A sponge device as claimed in claim 1 wherein said film layer plurality of holes have a diameter ranging from 0.10 to 0.70 mm.

3. A sponge device as claimed in claim 1 wherein said hydrophobic laminated layer is polarized.

4. A sponge device as claimed in claim 1 wherein said sterile sponge device body material is polyvinyl acetal.

5. A sponge device as claimed in claim 1 wherein said laminate film layer is polyethylene.

6. A sponge device as claimed in claim 1 wherein said laminate film layer is a halogenated polyolefin.

7. A sponge device as claimed in claim 6 wherein said halogenated polyolefin is polytetrafluoroethylene.

8. A sponge device as claimed in claim 1 wherein said laminated film layer is a polyester.

9. A sponge device as claimed in claim 8 wherein said polyester is a polyethylene terephthalate.

10. A sponge device as claimed in claim 1 wherein said sponge device is a nasal pack.

11. A sponge device as claimed in claim 1 wherein said sponge device is an otic pack.

12. A sponge device as claimed in claim 1 wherein said sponge device is an anal pack.

13. A sponge device as claimed in claim 1 wherein said sponge device is a vaginal pack.

14. A sponge device as claimed in claim 1 wherein said sponge device is a sinus pack.

15. A sponge device as claimed in claim 1 wherein said sponge device is a cervical pack.

16. A nasal surgical sponge device for placement into a nasal cavity comprising;

a sterile surgical sponge device body constructed of a compressed polyvinyl acetal open cell foam material having a pore diameter size which is greater than 0.004 mm but less than 1.2 mm and having instantaneous wicking properties causing the foam material to swell inside the nasal cavity and provide compression against the nasal cavity surface with the ability to absorb and retain at least 16 times its own weight in fluid, at least two wound engaging surfaces of said body being laminated with a smooth surfaced polymeric film layer about 0.0015 inch in thickness, each said polymeric film layer being pierced with a plurality of patterned holes less than 1.0 mm in diameter for fluid absorption into the body providing controlled absorbency into the polyvinyl acetal material while maintaining a substantially closed outer surface engaging the tissue reducing tissue attachment and device removal shear forces.

17. A surgical sponge device characterized by the ability be placed inside a natural body cavity and to absorb body fluid while precluding tissue attachment comprising;

a sterile surgical device body constructed of a polyvinyl acetal material having a substantially uniform pore diameter size generally ranging from 0.02 mm to 1.2 mm and instantaneous fluid wicking, opposing surfaces of said surgical device body being laminated with a smooth surfaced film layer ranging from 0.0005 to 0.0030 inches in thickness, said laminate film layers being provided with a plurality of throughgoing holes ranging from 0.10 to 0.70 mm to provide a film face having less than 15% of its area void allowing fluid access through the laminate film layer into the polyvinyl acetal body causing swelling of the body to form a self compression sponge supported in the cavity while reducing tissue attachment of said layers with said tissue of said cavity.

18. A sponge device as claimed in claim 17 wherein said holes are a plurality of slots.

19. A surgical sponge device for placement in an internal body cavity comprising;

a compressed sterile surgical device body constructed of an open cell polyvinyl acetal foam material having a substantially uniform pore diameter size which is not greater than 1.2 mm and having instantaneous wicking properties causing swelling of the foam material to take the shape of the internal body cavity, at least two surfaces of said body being laminated with a flexible hydrophilic polymeric film layer, each said polymeric film layer allowing fluid absorption through the film layer providing controlled absorbency and being formed with a substantially closed smooth outer surface reducing tissue attachment and device removal shear forces.

20. A surgical sponge device as claimed in claim 19 wherein said polymeric film layer is a polyolefin.

* * * * *